United States Patent [19]

Jang et al.

[11] Patent Number: 4,898,591
[45] Date of Patent: Feb. 6, 1990

[54] NYLON-PEBA COPOLYMER CATHETER

[75] Inventors: Yue-Teh Jang, Houston; Vern L. Liebmann, Sugar Land; Glenda S. Villman, Freeport, all of Tex.; Surendra A. Amin, Lake Charles, La.

[73] Assignee: Mallinckrodt, Inc., St. Louis, Mo.

[21] Appl. No.: 229,991

[22] Filed: Aug. 9, 1988

[51] Int. Cl.⁴ ............................................ A61M 25/00
[52] U.S. Cl. .................................... 604/282; 604/264
[58] Field of Search ............................... 604/280–282, 604/264; 128/348.1

[56] References Cited

U.S. PATENT DOCUMENTS

| | | | |
|---|---|---|---|
| 4,027,659 | 6/1977 | Slinglutt | 604/280 |
| 4,100,309 | 7/1978 | Micklus et al. | |
| 4,119,094 | 10/1978 | Micklus et al. | |
| 4,385,635 | 5/1983 | Ruiz | 128/658 |
| 4,425,919 | 1/1984 | Alston et al. | 604/282 |
| 4,531,943 | 7/1985 | Van Tassel et al. | |
| 4,551,292 | 11/1985 | Fletcher et al. | |
| 4,559,046 | 12/1985 | Groshong et al. | 604/282 |
| 4,563,181 | 1/1986 | Wijayarathna | 604/280 |
| 4,585,666 | 4/1986 | Lambert | 427/2 |
| 4,636,346 | 1/1987 | Gold et al. | 264/139 |
| 4,676,229 | 6/1987 | Krasnicki et al. | 128/4 |
| 4,790,831 | 12/1988 | Skribiski | 604/282 |

FOREIGN PATENT DOCUMENTS 0273618 7/1988 European Pat. Off. .
1600963 10/1981 United Kingdom .

OTHER PUBLICATIONS

1987 USCI publication.
Undated Shiley brochure.
Undated IMI publication.
Lorenz et al., "Use of Hydromer Coatings on Medical Devices", 10/4/84.

Primary Examiner—C. Fred Rosenbaum
Assistant Examiner—Mark O. Polutta
Attorney, Agent, or Firm—Bernard, Rothwell & Brown

[57] ABSTRACT

Inner and outer layers of a braided body portion of an intravascular catheter as well as a soft tip portion are formed from different proportioned blends of nylon and copolymer of ester linked polyethylene and polyamide to produce optimum mechanical properties in the catheter. One or more surfaces of the catheter are coated with a hydrogel containing a copolymer of polyurethane and polyvinylpyrrolidone to provide improved lubricity and antithrombogenicity.

18 Claims, 2 Drawing Sheets

NYLON-PEBA COPOLYMER CATHETER

BACKGROUND

1. Field of the Invention

The present invention relates to catheters which are inserted into blood vessels and are used for diagnostic purposes or for medical treatment.

2. Description of the Prior Art

Intravascular catheters are employed in medical applications for a variety of diagnostic and treatment procedures. These include the injection of radiopaque dye, the use of balloon catheters, the use of laser catheters, etc., in arteries in the heart, brain, abdominal and peripheral areas. Guiding catheters are used in placing balloon and laser catheters and other medical devices into the desired artery. Typically, the catheter being used in the diagnostic or treatment procedure, or the guiding catheter to be used for guiding the balloon or laser catheter, is inserted into an artery in the leg or arm of the patient and threaded, often with the aid of a guidewire in the catheter, through various arteries until the leading tip of the catheter reaches the desired location. The end of the catheter and/or the end of the guidewire is formed with a desired curvature so that by rotating the catheter about its longitudinal axis during insertion, the catheter can be inserted into the desired arterial branches to reach its destination. The tip or distal end section of the catheter is formed from a relatively flexible and soft material to avoid injury to the walls of the arteries and to enable flexing for insertion into the desired arterial branch.

The body portion of the catheter must have high torsion modulus and column strength with desired flexibility to negotiate a tortuous path through the arteries without buckling. The high torsion modulus or rigidity is needed to transmit rotary motion from the proximal end to the distal end of the catheter; with a relatively lower torsion modulus, rotation of the proximal end creates spring torsion force in the catheter until the resistance to rotation of the distal end is overcome and the distal end suddenly flips or rotates past its intended angle of rotation. Thus the higher the torsion modulus in the length of the catheter without changing flexibility, the easier it is for the physician to direct the catheter to its intended destination. High column strength or resistance to compression in the longitudinal direction is needed to enable the advancement of the catheter along the arteries or to advance medical devices in the guiding catheters against frictional resistance.

High torsion modulus and column strength can be produced in catheters by forming the body portion with a stainless steel braid between inner and outer tubular layers having desired flexibility, or by forming the body portion from a tubular material having the desired torsion and column rigidity. Typical materials employed in forming the inner and outer layers in prior art braided catheters include polyurethane or polyethylene. U.S. Pat. No. 4,563,181 to Wijayarathna et al. discloses forming the body portion of the catheter from nylon-11; a soft tubular tip formed from a blend of nylon-11 and an ester linked polyether-polyamide copolymer commonly known as polyether block amide (PEBA) is fused onto the distal end of the tubular body portion.

The use of a coating of hydrogel material including polyvinylpyrrolidone-polyurethane interpolymer on catheters to reduce insertion friction and to reduce thrombogenicity is disclosed in U.S. Pat. No. 4,100,309 to Micklus et al. The disclosed hydrogel material has been successfully coated on polyurethane catheters and silicone wound drains. It has been disclosed that the hydrogel material will also adhere to polyvinyl chloride, polymethyl methacrylate, polycarbonate, polyethylene terephthalate, polybutylene terephthalate, polytetramethylene terephthalate, latex rubber and polyisoprene. The hydrogel material can be applied to fluorocarbons and polyolefins which have been subjected to surface preparation to assure adequate wetting and bonding of the coating. The coating, when exposed to water, swells and develops a low coefficient of friction.

Although prior art intravascular catheters and the techniques for their employment have improved over the past several years, they have left a need for further improvement to enable optimization of catheter properties. Limited ranges of rigidity, flexibility and strength of materials possessing anti-thrombogenic and other blood compatible properties result in limitations on torsion modulus, column strength and flexibility of prior art intravascular catheters. Further the prior art catheters are subject to being expensive to manufacture.

Guiding catheters in particular require inner surfaces having a low coefficient of friction so that guidewires, balloon catheters, laser catheters, and other medical devices can be easily inserted and positioned in the arteries of the heart, brain or abdominal areas. Conventionally, such catheters have an inner layer formed from a fluoro polymer, such as polytetrafluoroethylene, fluorinated ethylene propylene copolymer, or a perfluoroalkoxy resin. The outer layer of the catheters are usually made of polyurethane or polyethylene, and braid wires are often interposed between the two layers to provide a suitable torsion modulus and column strength.

Such prior art guiding catheters have several deficiencies such as being expensive, having a small lumen, and losing their mechanical properties. Because of the dissimilarity between the materials of the inner and outer layers, extra steps, such as etching and applying adhesives are required to try to bond the two layers. In addition, extrusion of fluoro polymers requires special equipment and environmental control. This results in increased costs. The fluoro/urethane and fluoro/ethylene composites are generally softer than other polymers used in catheter bodies, and thus thicker walls, for example 0.014 to 0.018 inches (0.35 to 0.46 mm), are needed to provide the desired mechanical strength. This reduces the maximum size of lumen for a given size of catheter outer diameter to limit the size of medical device and the amount of contrast medium that can pass through the catheter. Further, fluoro polymers soften at body temperature and lose rigidity and preformed curvature to make their use more difficult.

SUMMARY OF THE INVENTION

The invention is summarized in an intravascular catheter having a tubular body formed from inner and outer tubular layers with a strengthening braid interposed between the inner and outer layers wherein the inner and outer layers are formed from a blend of a nylon and an ester linked polyether-polyamide co-polymer in proportions selected to produce desired properties for the catheter, and a soft tubular tip formed from a blend of a nylon and an ester linked polyether-polyamide copolymer in proportions selected to produce a relatively flexible and soft tip.

In another aspect of the invention, a guiding catheter having an inner layer of a blend of a nylon and an ester linked polyether-polyamide co-polymer is coated on its interior surface with a lubricous hydrogel polymer material, such as a copolymer of polyurethane and polyvinylpyrrolidone or a copolymer of polyethylene oxide and polyhydroxyethyl methacrylate.

An object of the invention is to construct an intravascular catheter which can be manufactured with a wide variety of torsion and flexibility properties without changing tubular wall thickness.

Another object of the invention is to increase lubricity of intravascular catheters in general, and of guiding catheters in particular.

One feature of the invention is the discovery that blends of a nylon and an ester linked polyether-polyamide co-polymer can be formulated to produce a wide range of properties suitable for the inner and outer layers of a braided catheter.

Another feature of the invention is the discovery that a hydrogel having a copolymer of polyurethane and polyvinylpyrrolidone will adhere to blends of a nylon and an ester linked polyether-polyamide co-polymer to form intravascular catheters with superior lubricity and antithrombogenic properties.

An advantage of the invention is that manufacturing costs for intravascular catheters can be reduced.

Another advantage of the invention is that different optimum properties of torsion modulus, flexibility and lubricity for corresponding different catheters can be produced without reducing lumen to external diameter ratios or employing incompatible or greatly different materials for the different catheters.

Other objects, advantages and features of the invention will be apparent from the following description of the preferred embodiment taken in conjunction with the accompanying drawings wherein:

DESCRIPTION OF THE PREFERRED EMBODIMENTS

Figure 1:
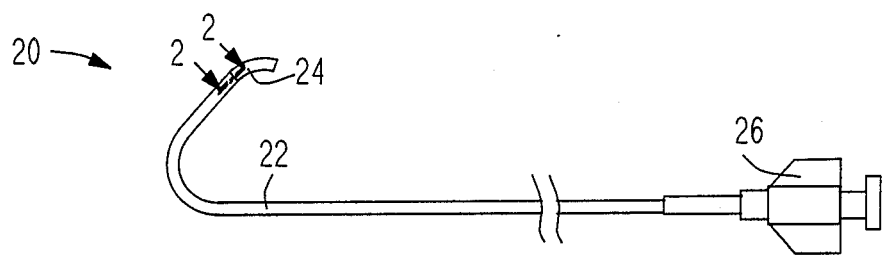
FIG. 1 is a side view of broken away distal and proximal end portions of a guiding intravascular catheter in accordance with the invention.
Figure 2:
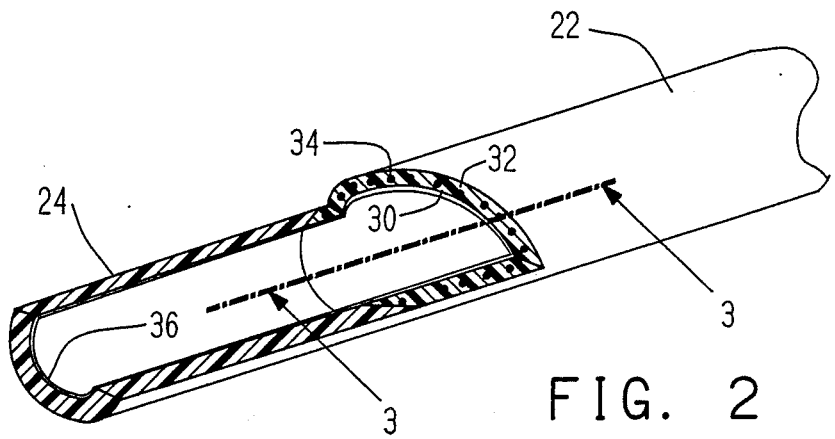
FIG. 2 is a perspective view of a broken away portion of the catheter of FIG. 1 with a section taken at line 2—2 in FIG. 1.
Figure 3:
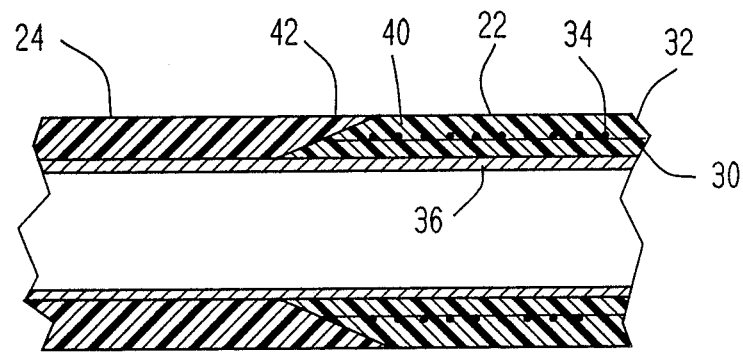
FIG. 3 is a side sectional view taken at line 3—3 in the broken away portion of FIG. 2.

As shown in FIG. 1, one embodiment of the invention is a guiding catheter indicated generally at 20 which has a tubular body 22 and a soft tip 24 attached to the distal end of the body. Conveniently a luer 26 is attached to the proximal end of the tubular body 22. As shown in FIGS. 2 and 3, the body 22 is formed with inner layer 30 and outer layer 32 between which is embedded a reinforcing braid 34. The inner and outer layers 30 and 32 and the soft tip 24 are all formed from blends of a nylon and an ester linked polyether-polyamide copolymer in proportions selected to produce desired properties for the catheter. Additionally, a lubricous hydrogel coating 36 is bonded on the inner surfaces of the catheter.

The nylon employed in the blended material is unplasticized nylon-11. Nylon-11 has been employed by itself to form a catheter body portion having suitable torsion modulus, flexibility and column strength. However, nylon-11 offers no range of modulus and flexibility properties for enabling the torsion modulus and flexibility properties to be changed for different catheters without changing the tubular wall thickness.

Blending of nylon-11 with an ester linked polyether-polyamide co-polymer to produce a soft flexible tip material which is fusible with nylon-11 is disclosed in U.S. Pat. No. 4,563,181 to Wijayarathna et al. It is now discovered that a blend of nylon-11 with an ester linked polyether-polyamide copolymer can also be used with a reinforcing braid to form a catheter body portion with optimum torsion modulus and flexibility properties. Furthermore different percentages of nylon-11 and copolymer in the blend can be selected for different catheters and for the inner and outer layers in the catheter body to optimize the physical properties of the different catheters. Since physical properties of different catheters can be optimized by only changing the proportions of nylon-11 and copolymer, manufacture of the different catheters is simplified and rendered less expensive. This contrasts with the prior art where either the physical properties of the different catheters were compromised, or costly manufacturing facilities for different materials had to be employed.

The ester linked polyether-polyamide co-polymer material is commonly known as polyether block amide (PEBA). This copolymer is chemically represented as:

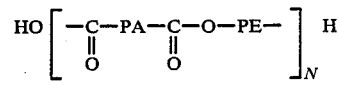

where PA is a polyamide and PE is a polyether and where N is an integer greater than 1 representing the number of blocks of co-polymer molecular units within the molecular formula of the copolymer. The copolymer is commercially available in a variety of molecular weights or formulations which are designated by their physical properties such as Shore hardness, tensile strength, and elongation. Copolymers of polyamide and polyether having a Shore hardness in the range from 25D to 70D are generally suitable for use in guiding catheters. Preferred PEBA copolymers for blending with nylon-11 to form flexible tips have a Shore hardness in the range from 25D to 55D, and preferred PEBA copolymers for blending with nylon-11 to form the inner and outer layers of body portions have a Shore hardness in the range from 40D to 65D.

Nylon-11 and PEBA. copolymer can be blended with the PEBA copolymer being in the range from 10 to 90 percent by weight of the mixture to form the blends used to make the tip, inner body layer and outer body layer of the catheter. For the soft flexible tip 24, the nylon-PEBA blend preferably includes from 50 to 90 percent by weight PEBA copolymer, and for the layers 30 and 32, the nylon-PEBA blend preferably includes from 30 to 90 percent by weight PEBA copolymer. The percentages of the PEBA copolymer in the respective layers 30 and 32 can be selected different in order to optimize the properties of the catheter. Higher percentages of PEBA copolymer in the outer layer 32 increase flexibility of the catheter body, but also decrease torsion modulus and column strength. Lower percentages of PEBA copolymer in the inner layer 30 can compensate for some of the decrease in torsion modulus and column strength. Conversely, lower percentages of PEBA copolymer in the outer layer 32 produce increased torsion modulus and column strength. Generally a lower percentage of PEBA copolymer in the inner layer 30 will provide structural strength to support the braid 34 during its winding with minimum wall thickness.

Optionally the polymer blend or blends in the tip 24, inner layer 30 and/or outer layer 32 can be made radiopaque by mixing the blend or blends with a radiopaque material. Suitable radiopaque materials which can be mixed with the polymer blends include bismuth subcarbonate, barium sulfate, bismuth trioxide and bismuth oxychloride. Generally, such radiopaque materials form from 5% to 50% by weight of the mixture.

The reinforcing braid 34 is any suitable strand material having high tensile strength and which can be wound on the inner tube layer 30 to form a braid which is then covered by extrusion of the outer layer. One suitable strand material is stainless steel wire. Other suitable materials for forming braid strands include aramids, such as that sold under the trademark KEVLAR by E. I. Du Pont, and nickel-chromium alloys.

The lubricous hydrogel coating 36 is a biocompatible material such as a copolymer of polyurethane and polyvinylpyrrolidone or cross-linked copolymer of polyethylene oxide and polyhydroxyethyl methacrylate. The hydrogel material is commercially available in solutions having from 1 to 3 parts by weight polyvinylpyrrolidone to 1 part polyurethane. Preferred hydrogel materials for catheters have 2 to 3 parts by weight polyvinylpyrrolidone to 1 part polyurethane. The hydrogel copolymer is dissolved in a mixture of liquid organic solvents and is applied by flushing the solution through the lumen of the catheter or by dipping the catheter in a bath of the solution or by spraying the solution onto the surfaces of the catheter insuring that all of the inner surface of the catheter is contacted with the solution to form a thin layer. Dipping and spraying also allow the outer surface to be coated. The liquid layer is then dried and cured in an oven forming the layer 36 which is about 1 mil (0.025 mm) thick. The layer 36, when wetted with water such as during flushing of the catheter with saline solution or X-ray contrast medium before placing in use, swells and becomes slippery.

In an example of a guiding catheter having an 8 French size, i.e. outside diameter of 0.105 inches (2.67 mm), the inner layer 30 is formed by extrusion in a conventional manner of a blend of 60% by weight nylon-11 and 40% by weight PEBA copolymer which has a Shore hardness of 55D to form a tube having a lumen diameter in the range from 0.078 to 0.082 inches (1.98 to 2.08 mm) and a wall thickness in the range from 0.004 to 0.006 inches (0.10 to 0.15 mm). Stainless steel wires are wound on the tube to form a braid. A sheath of a blend of 60% by weight nylon-11 and 40% by weight PEBA copolymer with a Shore hardness of 55D is then extruded in a conventional manner to form the outer layer 32 resulting in a tubular body 22 having the embedded braid 32. The soft tip 24 is a section of tube having a lumen diameter from 0.078 to 0.082 inches (1.98 to 2.08 mm) and an external diameter of 0.104 inches (2.67 mm) formed by extrusion of a blend of 15% by weight nylon-11 and 85% by weight PEBA copolymer which has a Shore hardness of 40D in a conventional manner The body and the tip are bonded together thermally and/or chemically. In the example shown in FIGS. 2 and 3, the bonded edges are initially formed with mating tapered edges so as to provide increased bonded surface areas to increase the strength of the bond. The lumen of the catheter is flushed with a solution of polyurethane and polyvinylpyrrolidone copolymer in a mixture of organic solvents, after which the catheter is air-dried before being thermally cured. Subsequently the distal end portion of the catheter is formed into its desired curvature, for example by inserting a mandrel or wire form of the desired shape and the catheter is again heated in an oven to a temperature of about 100°–160° C. for up to ten minutes and then cooled to set the desired shape of the catheter. A luer 26 is then attached in a conventional manner either before or after curving. The catheter may then be sterilized and packaged in a sealed package for sale and subsequent use.

Figure 4:
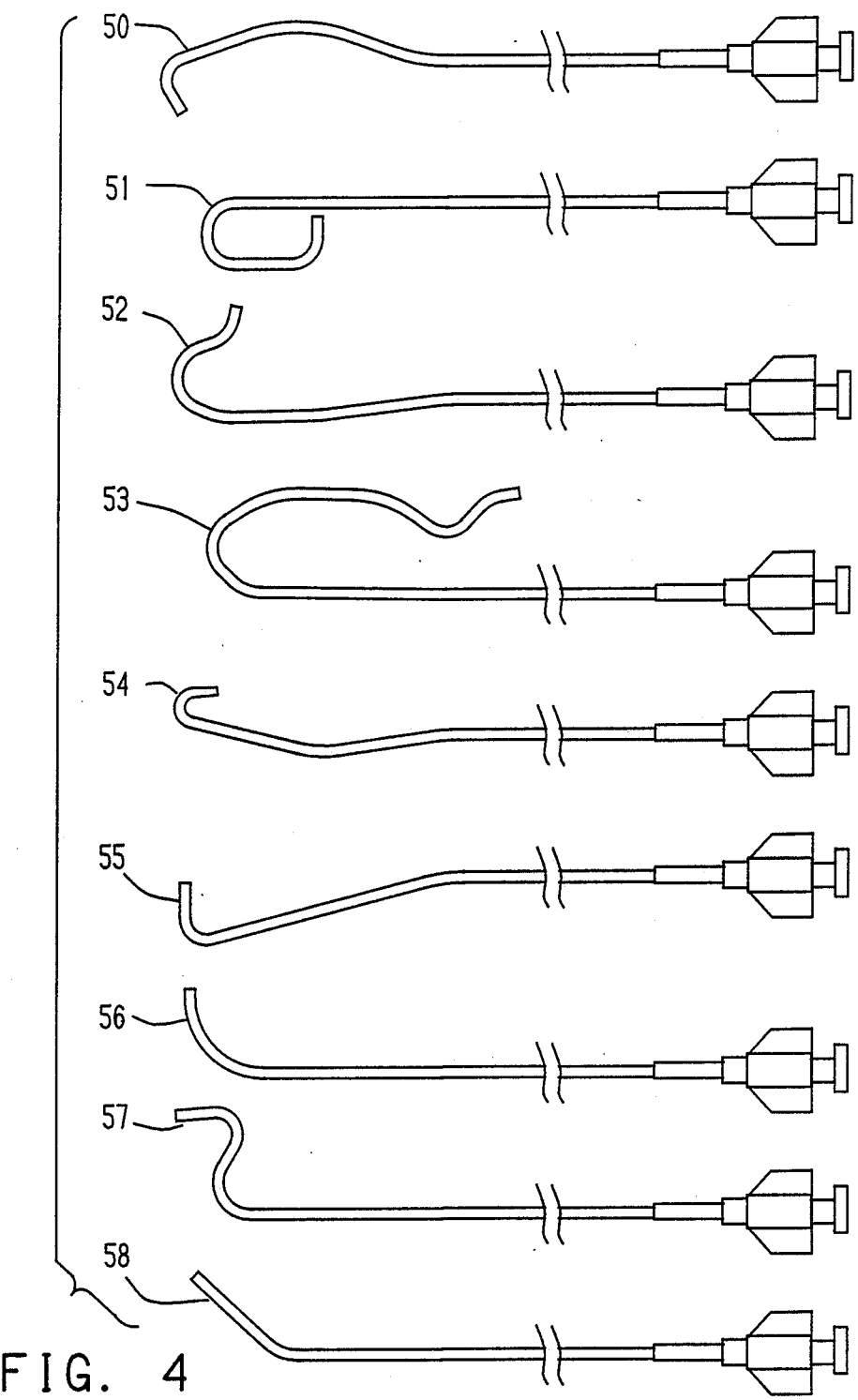
FIG. 4 is a side view of several intravascular catheters having different curvatures in their distal portions.

As illustrated in FIG. 4 by catheters 50, 51, 52, 53, 54, 55, 56, 57 and 58, intravascular guiding catheters are manufactured with a variety of different tip curvatures and lengths to meet various corresponding needs for catheterization of different arteries or for use by physicians who prefer a particular curvature.

While above described catheters have been guiding catheters, the invention can also be employed in other types of intravascular catheters, such as diagnostic or medical treatment catheters used with or without guiding catheters. Guiding catheters are generally made in sizes of 7 and 8 French (2.3 and 2.7 mm outer diameters), but other intravascular catheters are made in sizes down to 4 French (1.3 mm outer diameter). Also such catheters may have the hydrogel coating formed only on the exterior surface such as by spraying the solution of hydrogel material.

Since many variations, modifications, and changes in detail may be made to the above described embodiments, it is intended that all matter described above and shown in the accompanying drawings be interpreted as only illustrative of the invention and not in a limiting sense.

What is claimed is:

1. An intravascular catheter comprising
   a tubular body formed with inner and outer polymer layers with a reinforcing braid layer formed between the inner and outer layers, and
   a soft flexible tubular tip formed from a polymer and having one end bonded to an end of the tubular body,
   said polymers of said inner and outer layers and said tip including a blend of nylon and a copolymer of ester linked polyethylene and polyamide.

2. A catheter as claimed in claim 1 wherein the nylon is nylon-11 and the ester linked copolymer of polyethylene and polyamide is polyether block amide.

3. A catheter as claimed in claim 2 wherein the polyether block amide has a Shore hardness in the range from 25D to 70D, and the blend includes from 10 to 90% by weight of the copolymer of ester linked polyethylene and polyamide.

4. A catheter as claimed in claim 3 wherein the blend in the polymer of the inner and outer layers includes from 30% to 90% by weight of a copolymer of ester linked polyethylene and polyamide having a Shore hardness in the range from 40D to 65D, and the polymer of the tip includes from 50% to 90% by weight of a copolymer of ester linked polyethylene and polyamide having a Shore hardness in the range from 25D to 55D.

5. A catheter as claimed in claim 1 further including a coating of lubricous hydrogel on at least one surface of the catheter.

6. A catheter as claimed in claim 1 wherein the catheter is a guiding catheter, and the coating of lubricous hydrogel is formed on the interior surface of the catheter.

7. A catheter as claimed in claim 6 wherein the lubricous hydrogel material is a copolymer of polyurethane and polyvinylpyrrolidone.

8. A catheter as claimed in claim 7 wherein the copolymer of polyurethane and polyvinylpyrrolidone includes from 2 to 3 parts by weight polyvinylpyrrolidone to each part of polyurethane.

9. A catheter as claimed in claim 1 wherein at least one of the polymers of the inner and outer layers and the tip includes a radiopaque material.

10. A catheter as claimed in claim 9 wherein the radiopaqaue material is selected from the group consisting of bismuth subcarbonate, barium sulfate, bismuth trioxide and bismuth oxychloride.

11. A catheter as claimed in claim 9 wherein the polymer of the tip includes from 5% to 50% by weight radiopaque material.

12. A catheter as claimed in claim 9 wherein the polymer of one of the inner and outer layers of the tubular body includes from 5% to 50% by weight radiopaque material.

13. A catheter as claimed in claim 1 wherein the bonded ends of the tubular body and the tubular tip have mating tapered edges.

14. An intravascular catheter comprising
a tubular body formed from a polymer,
a soft flexible tubular tip formed from a polymer and having one end bonded to an end of the tubular body,
said polymers of said tubular body and said tip including a blend of nylon and a copolymer of ester linked polyethylene and polyamide, and
a coating of lubricous hydrogel on at least one surface of the catheter.

15. A catheter as claimed in claim 14 wherein the catheter is a guiding catheter, and the coating of lubricous hydrogel is formed on the interior surface of the catheter.

16. A catheter as claimed in claim 14 wherein the lubricous hydrogel material is a copolymer of polyurethane and polyvinylpyrrolidone.

17. A catheter as claimed in claim 16 wherein the copolymer of polyurethane and polyvinylpyrrolidone includes from 2 to 3 parts by weight polyvinylpyrrolidone to each part of polyurethane.

18. An intravascular catheter comprising
a tubular body comprising inner and outer polymer layers with a reinforcing braid layer between the inner and outer layers, and
a soft flexible tubular tip formed from a polymer and having one end attached to an end of the tubular body,
said polymer of said inner and outer layers and said tip comprising a copolymer of ester linked polyethylene an polyamide.

* * * * *

UNITED STATES PATENT AND TRADEMARK OFFICE
CERTIFICATE OF CORRECTION

PATENT NO. : 4,898,591

DATED : February 6, 1990

INVENTOR(S) : Yue-Teh Jang, et al.

It is certified that error appears in the above-identified patent and that said Letters Patent is hereby corrected as shown below:

Col. 5, line 64, after "manner" insert a period --.--.

Col. 8, line 27, "polymer" should be --polymers--.

Signed and Sealed this

Fifth Day of March, 1991

Attest:

HARRY F. MANBECK, JR.

*Attesting Officer*     *Commissioner of Patents and Trademarks*